CHRYSANTHEMUM PLANT
Filed Jan. 29. 1973
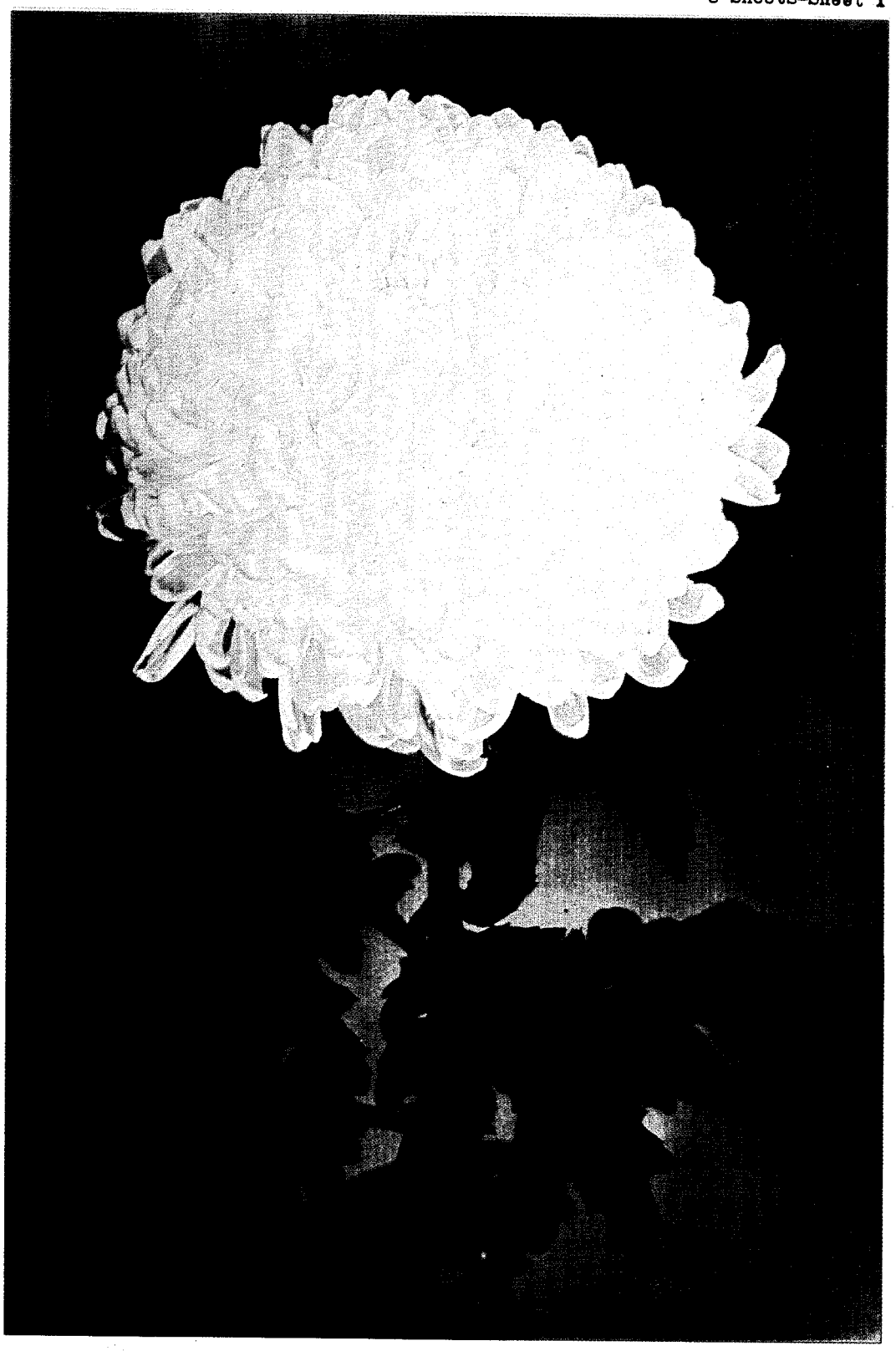

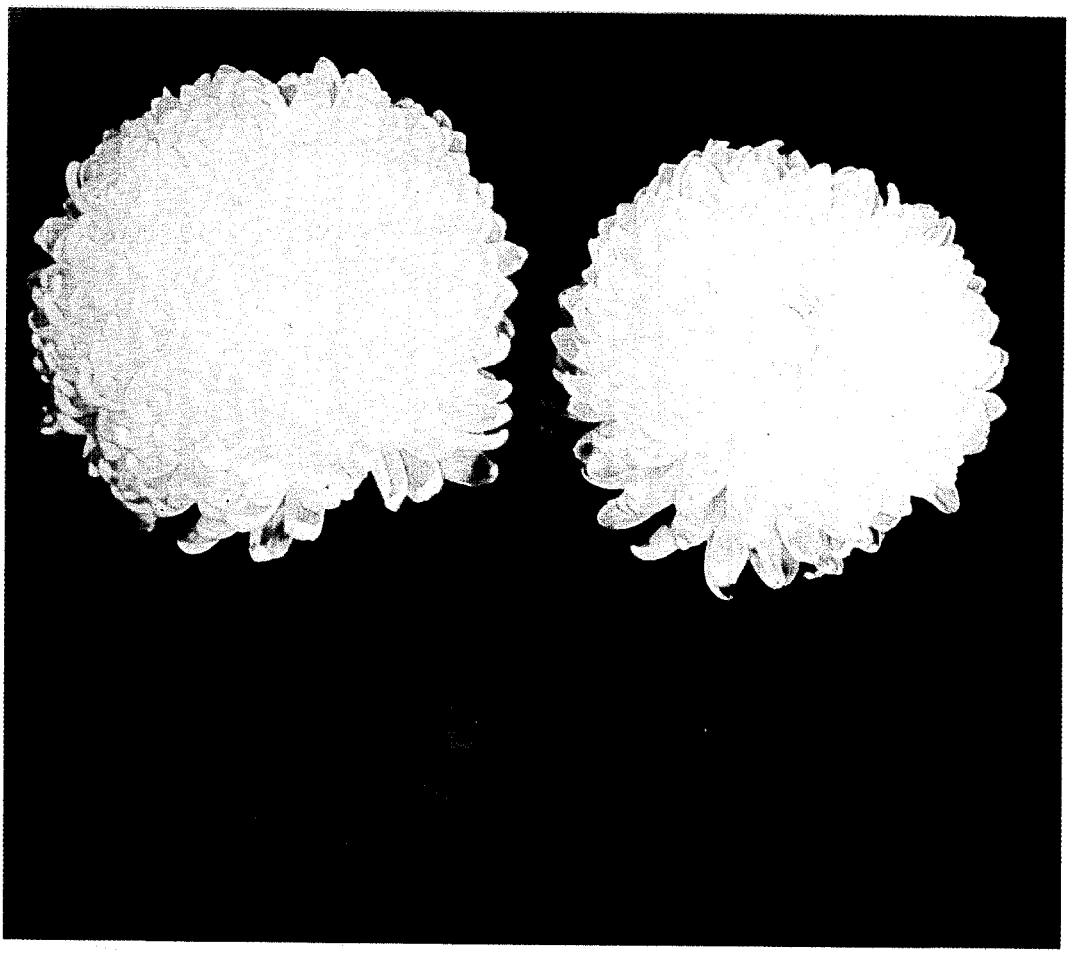

CHRYSANTHEMUM PLANT
Filed Jan. 29, 1973 3 Sheets-Sheet 3
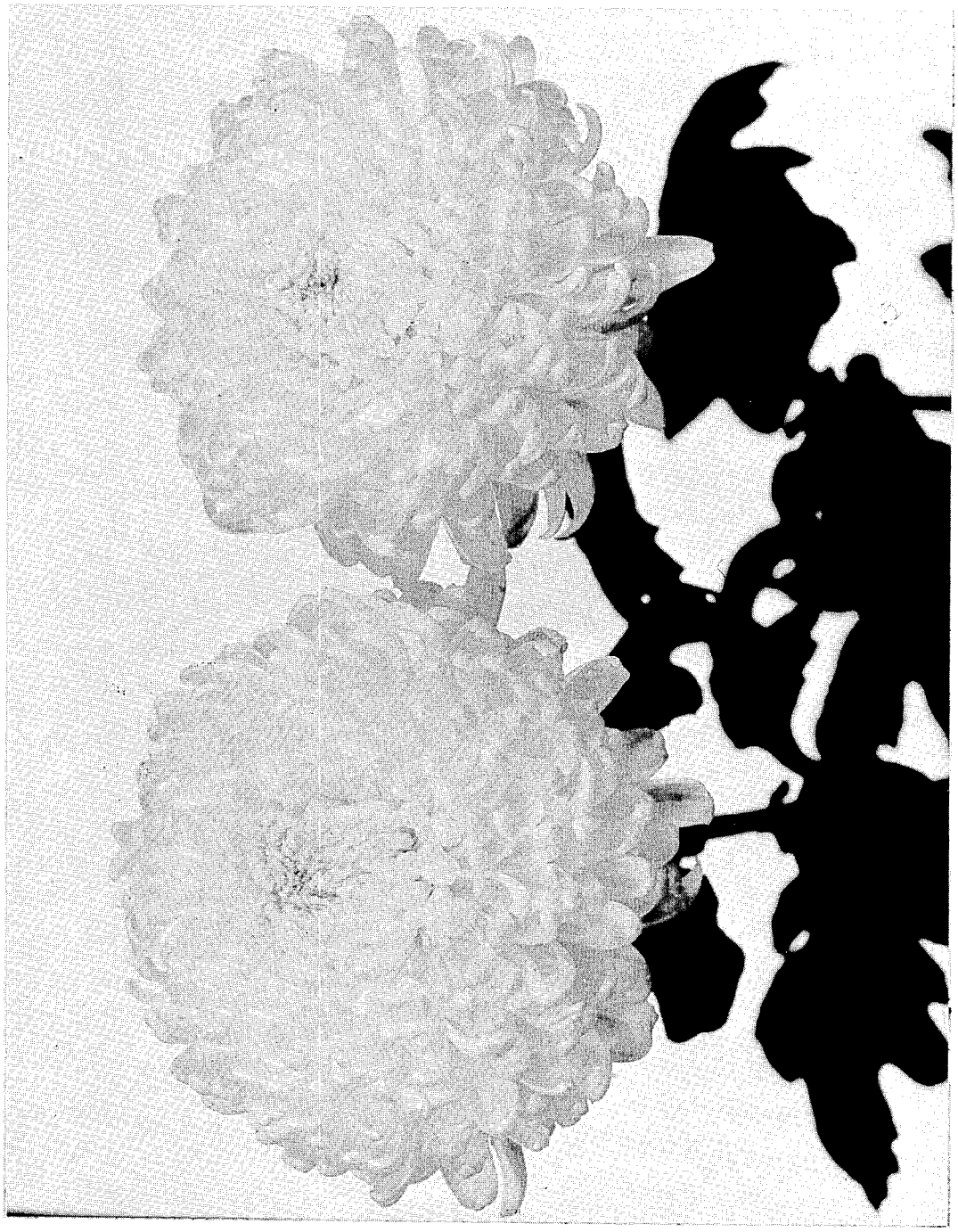

United States Patent Office

Plant Pat. 3,605
Patented Sept. 3, 1974

3,605
CHRYSANTHEMUM PLANT

Walter H. Jessel, Jr., Doylestown, and William E. Duffett, Akron, Ohio, assignors to Yoder Brothers, Inc., Barberton, Ohio

Filed Jan. 29, 1973, Ser. No. 327,806
Int. Cl. A01h *5/00*
U.S. Cl. Plt.—77 1 Claim

The present invention comprises a new and distinct cultivar of standard form chrysanthemum plant known by the varietal name Colonel Comfort. The new cultivar is a sport of the well known non-patented cultivar known in the United States as Southern Comfort.

The new cultivar is similar in many respects to Southern Comfort, having the same characteristics of:

1. Ivory flower color.
2. Sharp and reliable response at temperatures above 70°.
3. Similar foliage shape, color and form.
4. Similar recommended flowering period.

The new cultivar is distinguished from Southern Comfort by the following characteristics when grown under comparable conditions:

1. A flower approximately 1" to 1½" larger in diameter.
2. Based on Society of American Florists grading standards, it grades out with a higher percentage of flowers in the top two grades.
3. A more incurved flower form.
4. Approximately 2–3 days later response.
5. An improved form retention which provides longer bench life.
6. Foliage approximately ½" longer in length and ½" greater in width.

The new cultivar was selected from a flowering block of the parent cultivar at Barberton, Ohio, and when asexually reproduced by cuttings at Barberton, Ohio, has been found to retain its distinctive characteristics through successive propagations.

The new cultivar when grown in the vicinity of Barberton, Ohio, has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States is from mid-May through October, and in the southern United States, from April through mid-November.

The accompanying photographic drawings show the unique characteristics of the new cultivar, with the color being as nearly true as possible with color illustrations of this type. Sheet 1 of the drawings comprises a photograph of the new cultivar by itself. Sheet 2 comprises a comparison photograph, with the new cultivar appearing on the left and the parent cultivar Southern Comfort on the right. The difference in flower size and form retention is clearly illustrated. Sheet 3 is also a comparison photograph, in black and white, of the new cultivar, which appears on the left, and the parent cultivar Southern Comfort, which appears on the right. The difference in flower size is clearly apparent.

In the following description, color references are made to the Munsell Color Book, 1963 edition, and comparisons are made with the cultivar Southern Comfort. Where a value or description appears only for the new cultivar, the same value or description applies to the parent cultivar Southern Comfort.

Botanical classification: *Chrysanthemum morifolium*

| | Colonel Comfort | Southern Comfort |
|---|---|---|
| Bloom: | | |
| Size | 6½" | 5"–5½". |

Grade Data: Averaged Percentages for a Summer's Flowering Performance in 1972 at Barberton, Ohio, (based on Society of American Florists Grade Standards)

| | Blue | Red | Green | Culls |
|---|---|---|---|---|
| Colonel Comfort | 56% | 32% | 12% | |
| Southern Comfort | 35% | 41% | 14% | 10%. |

| | Colonel Comfort | Southern Comfort |
|---|---|---|
| Bloom (contd.): | | |
| Fully expanded | 7"–7½" | 6". |
| Borne | Singly on disbudded plant | |
| Stems | Strong | |
| Form | Semi-incurve | Semi-incurved but to a lesser degree. |
| Permanence | 12–14 days | 8–12 days. |
| Color: | | |
| Center of flower | Yellow-green, 1.25GY8/12 to yellow, 10Y8/12 | |
| Base of petals | Yellow, 10Y8/12 | |
| Inside of petals | Ivory, 10Y9/2 to ivory, 10Y9/1 | |
| Reverse of petals | Ivory, 10Y9/1 | |
| Tonality from a distance | Ivory white | |
| Discoloration | Ivory, 10Y9/1 | |
| Petals: | | |
| Texture | Smooth | |
| Appearance and form | Closed at base, flaring quickly to a smooth rounded keel tapering to a notched blunt tip. | |
| Arrangement | Composite, whorled on a single receptacle | |
| Persistence | Resist shatter | |
| Fragrance | Typical chrysanthemum | |
| Reproductive organs: | | |
| Stamen, anthers | None | |
| Pollen | do | |
| Arrangement | Clustered in center of flower, if present | |
| Styles | Present in ray florets | |
| Length | Short | |
| Ovaries | At the base of petal attached to receptacle | |
| Plant: | | |
| Form | Herbaceous | |
| Growth | Upright | |
| Height | Approximately 49"–58" given 2 long day weeks, and 11 week total crop time as defined in the timetables of Yoder Brothers, Inc., Barberton, Ohio, for the various seasons of the year. | Approximately 46"–54" given 2 long day weeks, and 11 week total crop time as defined in the timetables of Yoder Brothers, Inc., Barberton, Ohio, for the various seasons of the year. |
| Spread | None grown single stem | |

TABLE—Continued

| | Colonel Comfort | Southern Comfort |
|---|---|---|
| Foliage: | | |
| Top side | Dark green, 7.5GY2/4 | |
| Size | Length to width ratio 3/2 with foliage up to 6" long and 4" wide. | Length to width ratio 11/7 with foliage up to 5½" long, and 3½" wide. |
| Quantity | Numerous | |
| Shape | Spatulate lobed | |
| Texture | Coarse | |
| Ribs and veins | Prominent | |
| Edge | Indented | |
| Serration | Moderate | |
| Under side | Medium green, 7.5GY4/4 | |
| Stipules | Prominent | |

We claim:

1. A new and distinct cultivar of chrysanthemum characterized particularly as to uniqueness when compared to the parent cultivar Southern Comfort by its flower which is approximately 1"–1½" larger in diameter; by its superior grade performance, grading out with a higher percentage of flowers in the top two grades; approximately 3" to 4" more vigor; a more incurved flower form; approximately 2–3 days later response; improved form retention which provides longer bench life, and by its foliage which is approximately ½" longer in length and ½" greater in width.

No references cited.

ROBERT E. BAGWILL, Primary Examiner